(12) United States Patent
Win

(10) Patent No.: US 7,434,583 B2
(45) Date of Patent: Oct. 14, 2008

(54) LEG/ELBOW FIXING DEVICE

(76) Inventor: Jeff Win, No. 65, Tiansin Village, Yuanli Township, Miaoli County 358 (TW)

( * ) Notice: Subject to any disclaimer, the term of this patent is extended or adjusted under 35 U.S.C. 154(b) by 440 days.

(21) Appl. No.: 11/197,410

(22) Filed: Aug. 5, 2005

(65) Prior Publication Data

US 2007/0032756 A1 Feb. 8, 2007

(51) Int. Cl.
*A61F 5/24* (2006.01)
*A61F 5/37* (2006.01)
*A61F 5/00* (2006.01)

(52) U.S. Cl. .................... 128/881; 128/882; 128/121.1; 602/5; 602/12; 602/20; 602/23

(58) Field of Classification Search ......... 128/881–882, 128/878–879, 99.1, 121.1, 126.1; 602/5, 602/12, 16, 23–25, 27–28; 24/593.11, DIG. 47–48, 24/DIG. 43; 49/161–162, 240, 243, 245; 292/340, 341.14, 341.15, 341.17
See application file for complete search history.

(56) References Cited

U.S. PATENT DOCUMENTS

| 5,292,303 | A | * | 3/1994 | Bastyr et al. | 602/16 |
|---|---|---|---|---|---|
| 5,716,336 | A | * | 2/1998 | Hines et al. | 602/27 |
| 5,772,619 | A | * | 6/1998 | Corbett | 602/16 |
| 5,823,931 | A | * | 10/1998 | Gilmour | 602/24 |
| 6,108,821 | A | * | 8/2000 | Malsoute | 2/321 |
| 6,716,185 | B1 | * | 4/2004 | Rieger | 602/21 |
| 6,944,916 | B2 | * | 9/2005 | Kawagoe | 24/71 J |
| 7,097,627 | B2 | * | 8/2006 | Enzerink et al. | 602/23 |

* cited by examiner

*Primary Examiner*—Patricia Bianco
*Assistant Examiner*—Brandon Jackson
(74) *Attorney, Agent, or Firm*—Rosenberg, Klein & Lee

(57) ABSTRACT

A leg/elbow fixing device including a support bar having two connecting sections and two bracket assemblies fixable on the leg or elbow of a user. The bracket assemblies are adjustably located on the connecting sections of the support bar. Each bracket assembly includes a locating mechanism having a cavity in which the connecting section of the support bar is fitted. A receptacle is formed on top face of the cavity. A locating assembly is received in the receptacle. Each connecting section of the support bar is formed with notches. The locating assembly includes two arresting members each having a projecting block engaged with any of the notches of the support bar. The locating assembly further includes a restoring member compressed between the arresting members and a stop section. The stop section includes an upper cover and a cover member. The cover member is fixed in the receptacle for preventing the arresting members and restoring member from bounding out. The upper cover has two engaging blocks locked in the restricting holes of the arresting members for locating the bracket assemblies on the support bar.

10 Claims, 5 Drawing Sheets

LEG/ELBOW FIXING DEVICE

BACKGROUND OF THE INVENTION

The present invention is related to a leg/elbow fixing device which can be microadjusted for more firmly, more comfortably and more safely supporting and fixing a patient's leg or elbow.

Conventionally, a fractured limb of a patient is fixed with gypsum and bandage. After the fractured part of the patient is fixed with the gypsum, the gypsum will be a heavy burden to the patient and make the patient hard to conveniently move. Moreover, due to poor air-permeability, the fractured part of the patient often suffers heat, itch, allergy, etc. In addition, the gypsum has poor supporting strength and tends to break due to incautious bending or collision. Furthermore, the gypsum will be softened by water so that when contaminated, it is impossible to clean the surface of the gypsum with wet cloth. Also, the gypsum is custom-made for a specific patient with a specific configuration. The gypsum is not adjustable in length so that it is impossible to reuse the gypsum for any other patient with different configuration. According to the above, the gypsum can hardly provide sufficient supporting strength, convenience, comfortableness and safety for the patient.

Another type of conventional leg/elbow fixing device includes at least two board bodies or brackets fixable on outer side of the fractured part. The board bodies are wrapped and tied on the fractured limb with bandages for fixing the fractured limb. Such measure is also not adjustable in length and cannot be reused for another patient. Also, the board bodies cannot be quickly and conveniently detached.

SUMMARY OF THE INVENTION

It is therefore a primary object of the present invention to provide a leg/elbow fixing device which can provide firm support, comfortableness and safety for a patient. In addition, the leg/elbow fixing device can be quickly conveniently adjustably mounted on a fractured limb of the patient and easily detached therefrom. The leg/elbow fixing device includes a support bar and two bracket assemblies fixable on the leg or elbow of a user. The support bar is connected between the two bracket assemblies. Each bracket assembly includes a locating mechanism for adjustably locating the bracket assembly on the support bar.

According to the above object, the leg/elbow fixing device of the present invention includes a support bar having two connecting sections and two bracket assemblies fixable on two limbs connected by a joint of a user. The bracket assemblies are adjustably located on the connecting sections of the support bar. Each bracket assembly includes a locating mechanism for locating the bracket assembly on the support bar after adjusted.

The present invention can be best understood through the following description and accompanying drawings wherein:

DETAILED DESCRIPTION OF THE PREFERRED EMBODIMENT

Figure 1:
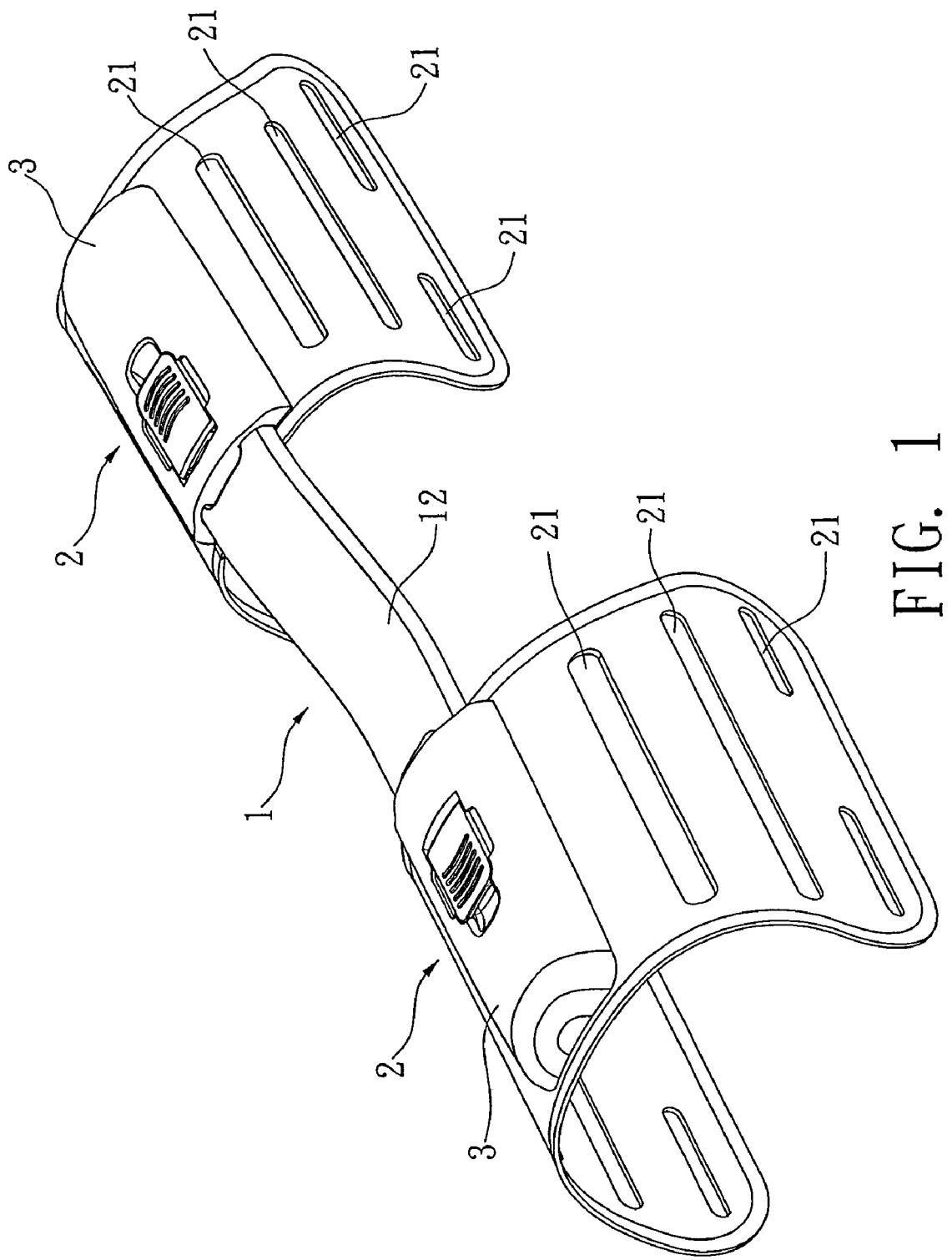
FIG. 1 is a perspective assembled view of the present invention.

Please refer to FIGS. 1 to 4. The leg/elbow fixing device of the present invention includes a support bar 1 having two connecting sections 11 at two ends. The support bar 1 further has a bent section 12 between the two connecting sections 11. The bent section 12 is formed according to human engineering, whereby there is a difference in height between the two connecting sections 11 for more snugly attaching to two limbs connected by a joint. Two sides of each connecting section 11 are formed with notches 13 at equal intervals.

The leg/elbow fixing device further includes two bracket assemblies 2. Two sides of each bracket assembly 2 are formed with several fixing slots 21. A movable bandage (not shown) can be passed through the engaging slots 21 to fix the bracket assemblies 2 on two limbs connected by a joint. Each bracket assembly 2 has a locating mechanism 3.

The locating mechanism 3 includes a cavity 31 corresponding to the connecting section 11 of the support bar 1. Accordingly, the two bracket assemblies 2 can be fitted on two ends of the support bar 1. A top face of the locating mechanism 3 is formed with a receptacle 32 communicating with the cavity 31. A locating assembly 4 is disposed in the receptacle 32 for locating the bracket assemblies 2 on the support bar 1 after adjusted.

A lifting section 323 is formed on one side of the opening of the receptacle 32. A rib 321 is disposed in and bridged over the receptacle 32. The rib 321 extends in a direction of the axis of the lifting section 323. Each of two ends of the rib 321 is formed with a fixing hole 322.

Figure 2:
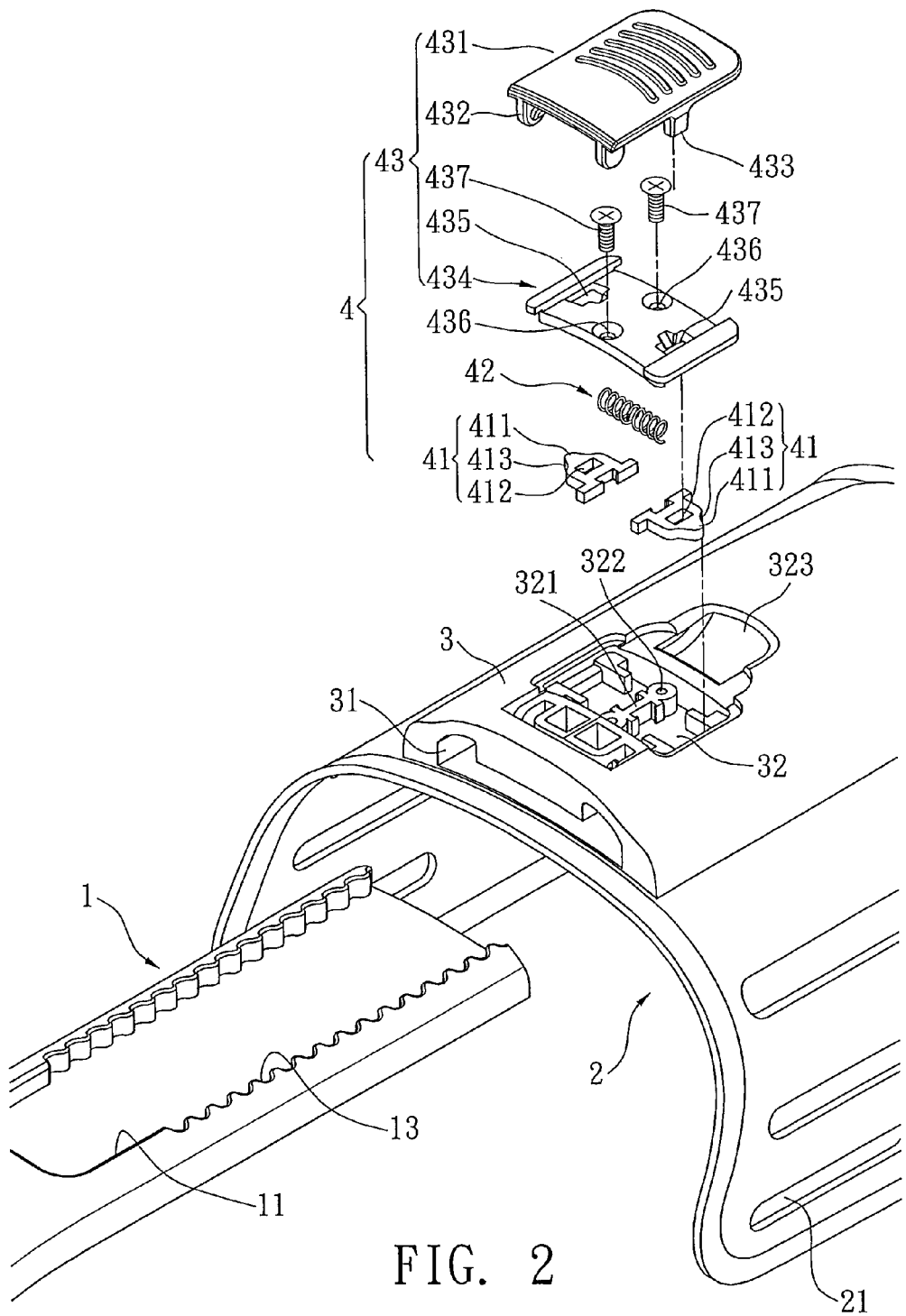
FIG. 2 is a perspective exploded view of the present invention, showing the support bar, bracket assembly and locating mechanism of the present invention.
Figure 3:
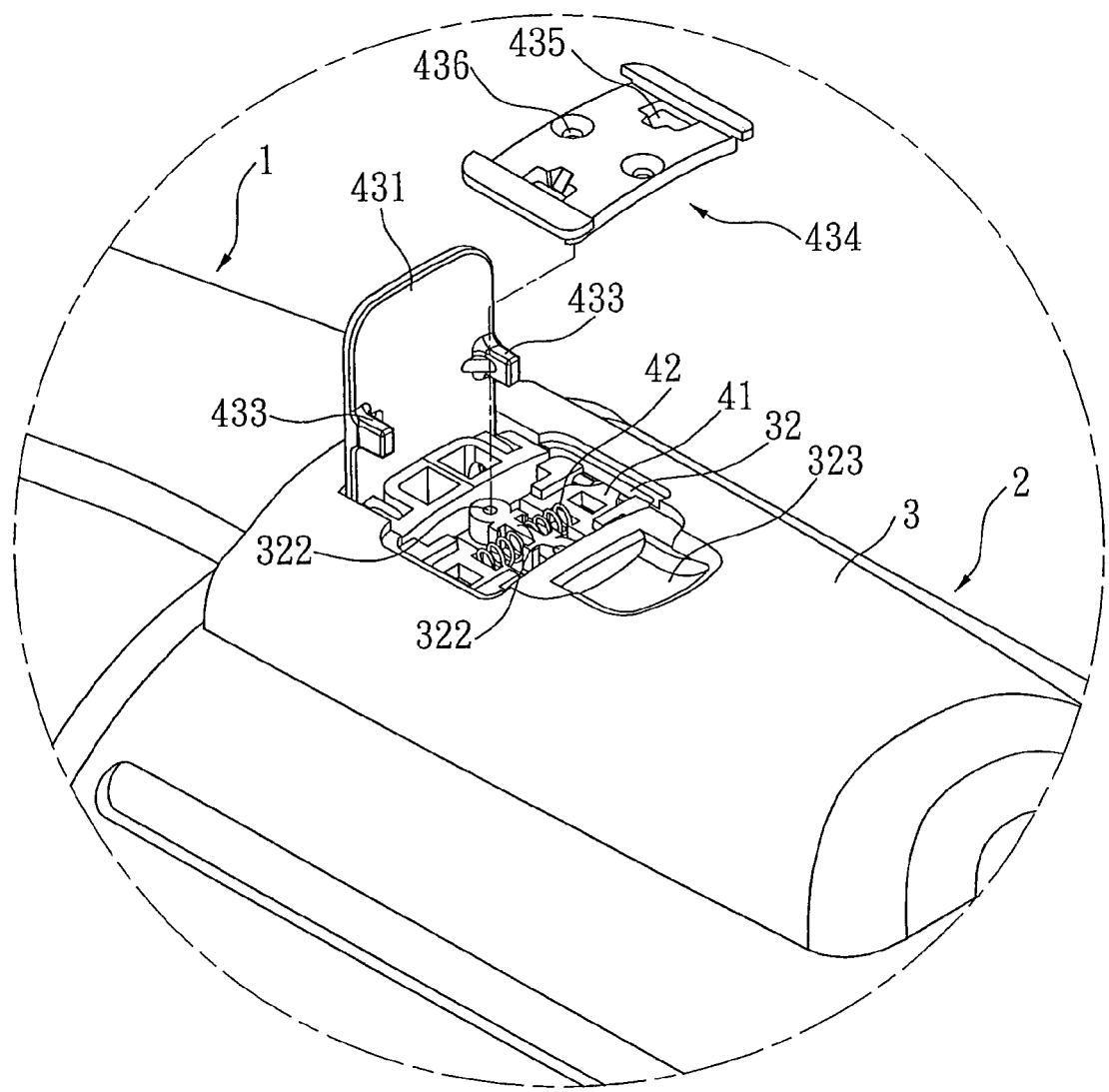
FIG. 3 is a perspective assembled view of the locating mechanism of the present invention, in which the upper cover is lifted and the cover member is detached.
Figure 4:
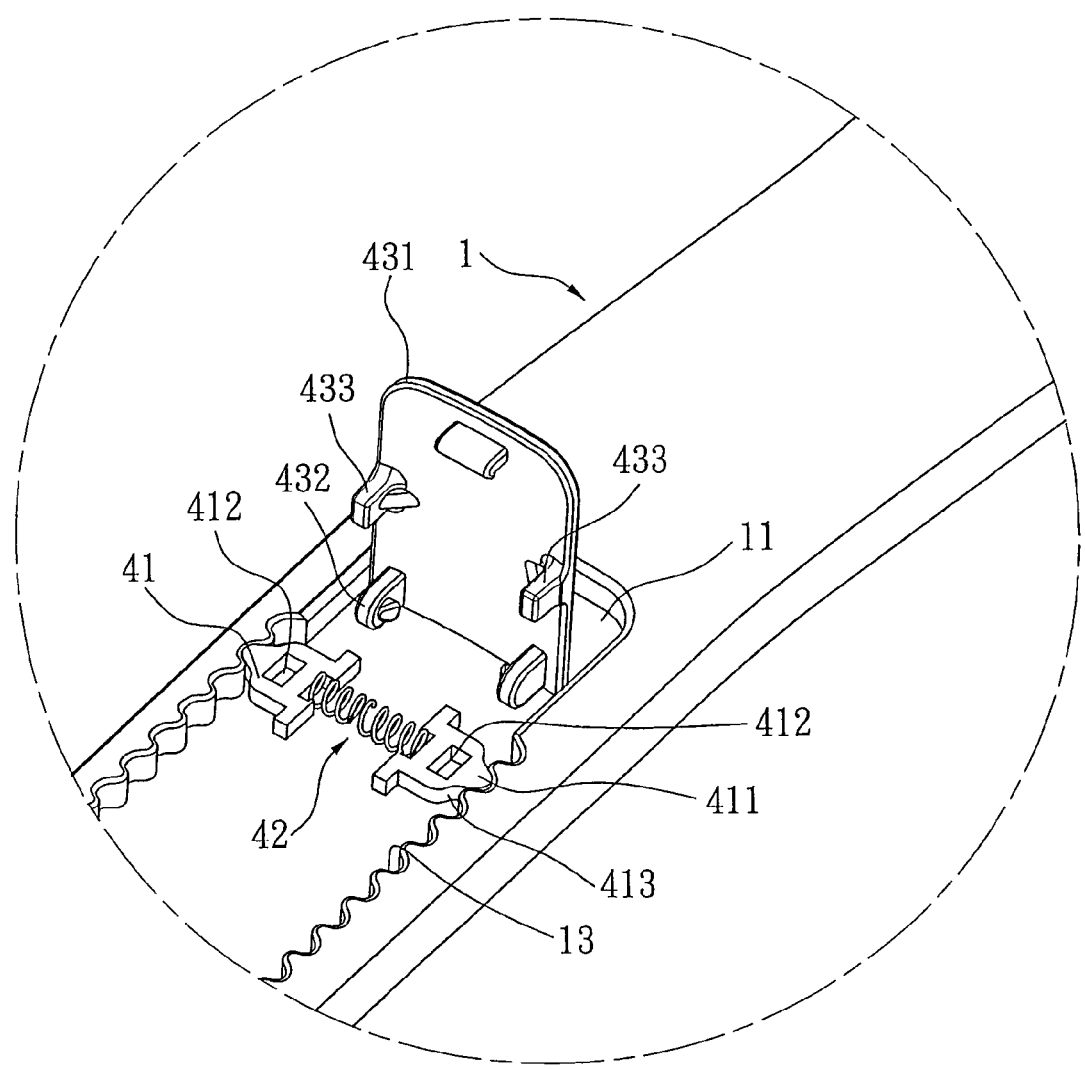
FIG. 4 shows the engagement between the arresting members and the notches of the support bar of the present invention.

Referring to FIGS. 2 and 3, the locating assembly 4 includes at least one arresting member 41, a restoring member 42 and a stop section 43. In this embodiment, the locating assembly 4 includes two opposite arresting members 41 and the restoring member 42 is a compression spring. One side of each arresting member 41 has a projecting block 411 facing the notches 13 of the support bar 1. The arresting members 41 are received in the receptacle 32. In this embodiment, the projecting block 411 has two lateral slopes 413, whereby the projecting block 411 has a shape corresponding to the shape of the notches 13 and can snugly engage with any of the notches 13 of the support bar 1. The middle section of the restoring member 42 perpendicularly intersects the rib 321 with the rib 321 inlaid in the restoring member 42. The restoring member 42 is compressed between the other sides of the arresting members 41 proximal to the rib 321. Each arresting member 41 is formed with a central restricting hole 412.

The stop section 43 includes an upper cover 431 having a pivot section 432 on one side for pivotally connecting the upper cover 432 with the other side of the opening of the receptacle 32. A bottom end of the upper cover 431 has at least one engaging block 433. In this embodiment, the upper cover 431 has two engaging blocks 433.

The stop section 43 further includes a cover member 434 formed with two first through holes 435 corresponding to the engaging blocks 433 of the upper cover 431. The engaging blocks 433 of the upper cover 431 can extend through the first through holes 435 of the cover member 434 to be fixed in the restricting holes 412 of the arresting members 41. Two fixing members 437 are extended through two second through holes 436 of the cover member 434 to be fixed in the fixing holes 322 of the rib 321 in the receptacle 32. In this embodiment, the fixing members 437 are bolts for fixing and preventing the locating assembly 4 from bounding out of the receptacle 32.

Figure 5:
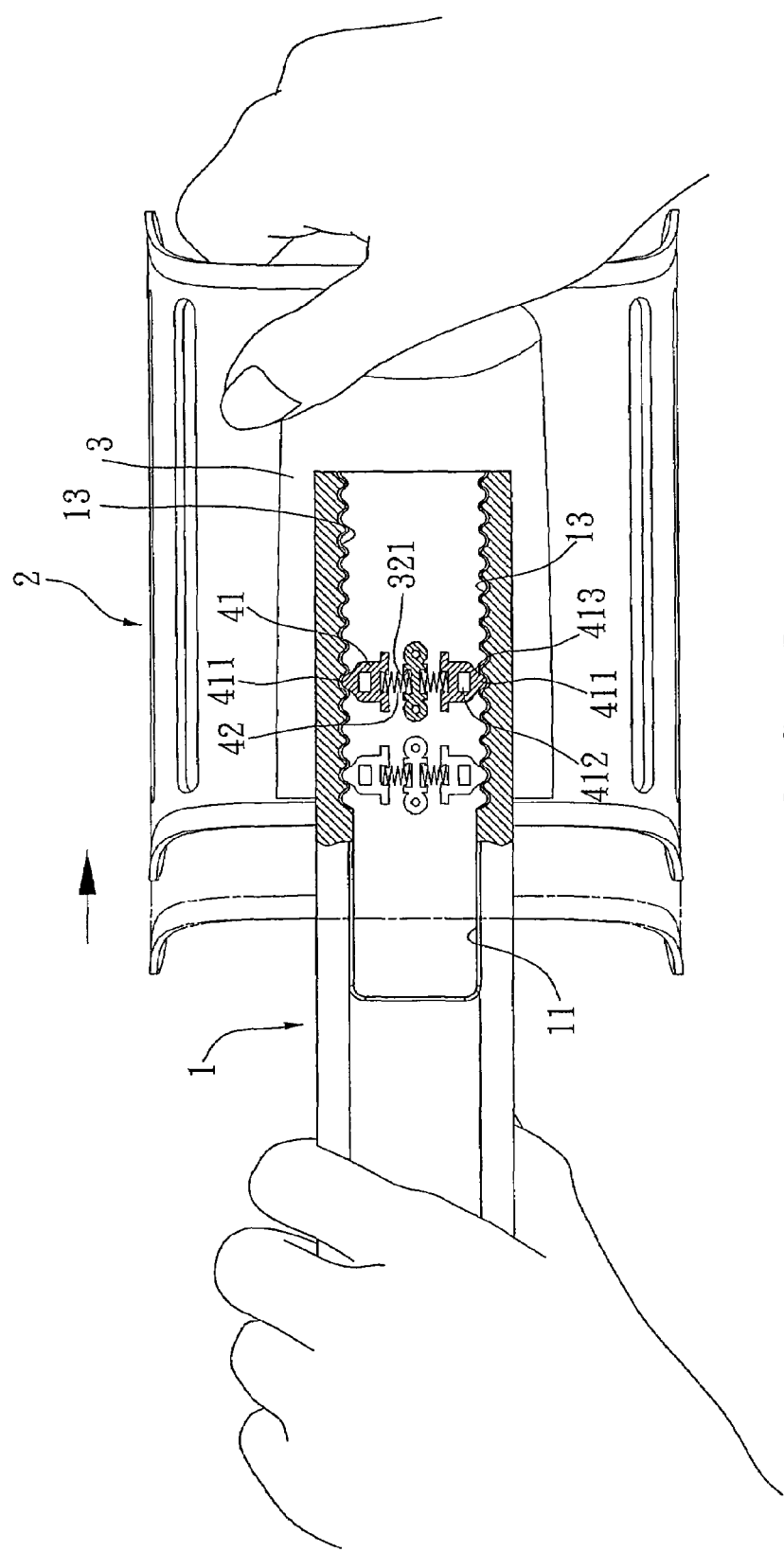
FIG. 5 shows the adjustment of the present invention.

Referring to FIG. 5, when adjusted, a user can first extend his/her finger into the lifting section 323 to lift the upper cover 431, making the engaging blocks 433 disengaged from the restricting holes 412 of the arresting members 41 and the first through holes 435 of the cover member 434. Then one of the bracket assemblies 2 is leftward pushed or rightward pulled. At this time, the bracket assembly 2 is transversely moved, whereby the projecting blocks 411 of the arresting members 41 can be easily disengaged from the notches 13 of the support bar 1 due to the slopes 413 of the projecting blocks 411. Under such circumstance, the arresting members 41 are longitudinally displaced to compress the restoring member 42. When the projecting blocks 411 are adjusted and moved to the next notches 13, the restoring member 42 pushes and restores the arresting members 41 to again engage with the notches 13. Finally, the upper cover 431 is closed with the finger. Under such circumstance, the engaging blocks 433 extend through the first through holes 435 of the cover member 434 to be locked in the restricting holes 412 of the arresting members 41. At this time, the adjustment is completed.

The above embodiment is only used to illustrate the present invention, not intended to limit the scope thereof. Many modifications of the above embodiment can be made without departing from the spirit of the present invention.

What is claimed is:

1. A leg/elbow fixing device comprising:
   a support bar, two ends of the support bar respectively having two connecting sections;
   two bracket assemblies fixable on two limbs connected by a joint of a user, each bracket assembly having a locating mechanism, whereby the bracket assemblies can be respectively slidably located on the connecting sections of the support bar, the locating mechanism including a cavity corresponding to the connecting section of the support bar, whereby the two bracket assemblies are fitted on two ends of the support bar, a top face of the locating mechanism being formed with a receptacle communicating with the cavity; and
   a locating assembly being disposed in the receptacle for locating the bracket assemblies on the support bar, the locating assembly including at least one arresting member, a restoring member and a stop section, one side of each arresting member having a projecting block facing notches formed in the support bar, the arresting members being received in the receptacle with the projecting block engaged with any of the notches of the support bar, a middle section of the restoring member perpendicularly intersecting a rib with the rib inlaid in the restoring member, the restoring member being compressed between the other sides of the arresting members proximal to the rib, each arresting member being formed with a central restricting hole, the stop section including an upper cover, the upper cover having a pivot section on one side for pivotally connecting the upper cover with another side of the opening of the receptacle, a bottom end of the upper cover having at least one engaging block, whereby the engaging block of the upper cover can extend through a first through hole formed in the cover member to be fixed in the restricting hole of the arresting member.

2. The leg/elbow fixing device as claimed in claim 1, wherein at least one side of each connecting section is formed with the notches at equal intervals.

3. The leg/elbow fixing device as claimed in claim 1, wherein the support bar further has a bent section between the two connecting sections, the bent section being formed according to human engineering.

4. The leg/elbow fixing device as claimed in claim 1, wherein two sides of each bracket assembly are formed with several fixing slots.

5. The leg/elbow fixing device as claimed in claim 1, wherein a lifting section is formed on one side of the opening of the receptacle, the rib being disposed in and bridged over the receptacle, the rib extending in a direction of an axis of the lifting section, the rib being formed with at least one fixing hole.

6. The leg/elbow fixing device as claimed in claim 1, wherein the restoring member is a compression spring.

7. The leg/elbow fixing device as claimed in claim 1, wherein the projecting block has two lateral slopes, whereby the projecting block has a shape corresponding to the shape of the notches.

8. A leg/elbow fixing device comprising:
   a support bar, two ends of the support bar respectively having two connecting sections;
   two bracket assemblies fixable on two limbs connected by a joint of a user, each bracket assembly having a locating mechanism, whereby the bracket assemblies can be respectively slidably located on the connecting sections of the support bar, the locating mechanism including a cavity corresponding to the connecting section of the support bar, whereby the two bracket assemblies are fitted on two ends of the support bar, a top face of the locating mechanism being formed with a receptacle communicating with the cavity; and
   a locating assembly being disposed in the receptacle for locating the bracket assemblies on the support bar, the locating assembly including at least one arresting member, a restoring member and a stop section, one side of each arresting member having a projecting block facing notches formed in the support bar, the arresting members being received in the receptacle with the projecting block engaged with any of the notches of the support bar, a middle section of the restoring member perpendicularly intersecting a rib with the rib inlaid in the restoring member, the restoring member being compressed between the other sides of the arresting members proximal to the rib, each arresting member being formed with a central restricting hole, the stop section further including a cover member, wherein the cover member is formed with at least one first through hole corresponding to the engaging block of the upper cover, whereby the engaging block of the upper cover can extend through the first through hole of the cover member to be fixed in the restricting hole of the arresting member.

9. The leg/elbow fixing device as claimed in claim 8, wherein two fixing members are extended through two second through holes of the cover member to be fixed in the fixing holes of the rib in the receptacle.

10. The leg/elbow fixing device as claimed in claim 9, wherein the fixing members are bolts.

* * * * *